United States Patent
Schilling et al.

[19]

[11] Patent Number: 5,951,545
[45] Date of Patent: Sep. 14, 1999

[54] HIGH-FREQUENCY SURGICAL INSTRUMENT AND METHOD OF OPERATING THE SAME

[75] Inventors: Bertram Schilling, Mauenheim; Udo Tockweiler, Immendingen; Wolfram Hill, Freiburg, all of Germany

[73] Assignee: Gebrueder Berchtold GmbH & Co., Tuttlingen, Germany

[21] Appl. No.: 08/892,872

[22] Filed: Jul. 15, 1997

[30] Foreign Application Priority Data

Jul. 15, 1996 [DE] Germany .............................. 19628428

[51] Int. Cl.$^6$ ................................................. A61B 17/39
[52] U.S. Cl. .................. 606/37; 606/39; 606/40
[58] Field of Search ................. 606/32–35, 37, 606/39, 40

[56] References Cited

U.S. PATENT DOCUMENTS

| | | |
|---|---|---|
| 4,739,759 | 4/1988 | Rexroth et al. . |
| 4,848,335 | 7/1989 | Manes . |
| 4,903,696 | 2/1990 | Stasz et al. ................................ 606/37 |
| 5,226,904 | 7/1993 | Gentelia et al. ........................... 606/42 |
| 5,540,682 | 7/1996 | Gardner et al. ............................ 606/37 |
| 5,540,683 | 7/1996 | Ichikawa et al. .......................... 606/40 |

FOREIGN PATENT DOCUMENTS

| | | |
|---|---|---|
| 0495140 A1 | 7/1992 | European Pat. Off. . |
| 0521501 A2 | 1/1993 | European Pat. Off. . |
| 0556705 A1 | 8/1993 | European Pat. Off. . |
| 2646229 | 4/1978 | Germany . |
| 3050386 C2 | 6/1987 | Germany . |
| 3923024 A1 | 2/1990 | Germany . |
| 4205213 A1 | 8/1993 | Germany . |
| 4233467 A1 | 4/1994 | Germany . |
| 4339049 A1 | 5/1995 | Germany . |

*Primary Examiner*—Linda C. M. Dvorak
*Assistant Examiner*—Roy Gibson
*Attorney, Agent, or Firm*—Townsend and Townsend and Crew LLP

[57] ABSTRACT

A high-frequency surgical apparatus has a plurality of different operating modes, such as monopolar, tripolar, bipolar, at least one function such as cutting, coagulation in each operating mode and at least one operating mode with several functions and also at least one characteristic within each function which can be selected by one switching key in each case. In accordance with the invention an operating mode selection key is provided for each operating mode. At least some of the switching keys are associated with several operating mode selection keys. On actuating at least one of the operating mode selection keys several of the switching keys are blocked.

12 Claims, 2 Drawing Sheets

HIGH-FREQUENCY SURGICAL INSTRUMENT AND METHOD OF OPERATING THE SAME

FIELD OF THE INVENTION

The invention relates to a high-frequency surgical apparatus having a plurality of operating modes, such as monopolar, tripolar, bipolar, and a plurality of switch keys which permit the selection of a specific number of individual characteristics for each operating mode with a desired, impedance dependent, radio-frequency voltage-current characteristic corresponding to one of the individual characteristics being fed in each of the operating modes to a high-frequency treatment instrument corresponding to the relevant operating mode.

Moreover, the invention relates to a high frequency surgical apparatus having a plurality of different operating modes, such as monopolar, tripolar, bipolar, and at least function such as cutting or coagulating, respectively associated with at least one operating mode wherein, on pressing one or more switching keys in each operating mode in each case, one of a plurality of characteristics is dialed in for each function in order to feed a treatment instrument corresponding to the selected operating mode with a high-frequency current-voltage characteristic desired for a particular treatment from a plurality of impedance dependent, high-frequency, current-voltage characteristics corresponding to the number of characteristics.

The invention also relates to a high-frequency surgical apparatus having a plurality of different operating modes, such as monopolar, tripolar, bipolar, at least one function such as cutting or coagulating in each operating mode, at least one operating mode with a plurality of functions and also at least one characteristic within each function which can in each case be dialed in by a switching key.

DESCRIPTION OF PRIOR ART

High-frequency surgical apparatus of this kind should be capable of universal use for the most diverse purposes. For this purpose, a high-frequency surgical apparatus has connections for one or more monopolar, bipolar and/or tripolar high-frequency surgical instruments and also for the connection of a neutral electrode. Under tripolar instruments, one understands those in which the neutral electrodes are located at the instrument itself and with which a coagulation or a cutting process can be selectively carried out in that the instrument is connected in three-pole manner to the high-frequency generator, which makes it possible to selectively effect a bipolar coagulation or a bipolar cutting by means of two coagulation electrodes or by means of a neutral electrode and a cutting electrode of the instrument.

Moreover, a foot switch is generally also connected to the apparatus with which the instrument being used can be selectively switched on or off.

The internal circuit of such high-frequency surgical apparatus is in this respect generally such that with the simultaneous connection of several instruments in each case only one can be operated at any one time, whereas the other is automatically switched off. That instrument which is first switched on thereby has preference.

With such a high-frequency surgical apparatus, numerous switching and display possibilities must be present for the different applications, so that the surgeon, depending on the instrument used, can set the desired operating mode, for example monopolar, tripolar or bipolar, the function such as cutting or coagulating and finally the desired characteristic of the high-frequency current-voltage plot. As a result of these manifold switching and display possibilities the operating fields or panels of such high-frequency surgical apparatus are frequently very confused so that their use requires a high degree of concentration, and problems can arise because of operator error.

OBJECT OF THE INVENTION

The object of the present invention is to provide a method and a high-frequency surgical apparatus of the initially named kind which has a very clear actuating and display field or panel, but which nevertheless permits a large number of different switching and display possibilities such as are required for universal use of the apparatus.

BRIEF DESCRIPTION OF THE INVENTION

In order to satisfy this object there is provided, in accordance with a first variant of the invention, a method in which at least one and preferably a plurality of switching keys are associated with a plurality of operating modes and in which a predetermined proportion or number of the switching keys can be selected in each operating mode and the rest of the switching keys are blocked.

In accordance with a second variant of the invention, there is provided a method in which the switching keys are at least partially associated with more than one operating mode; in which at least one of the operating modes is selected, in which an individual characteristic can be dialed in with each switch key, depending on the operating mode with which it is associated, or the switching key is blocked, and in which, of the switching keys which are not blocked, those which result in a desired characteristic can be pressed.

Furthermore, in accordance with a third aspect of the invention, there is provided a high-frequency surgical apparatus in which an operating mode selection key is provided for each operating mode; in which at least a proportion of the switching keys is associated with a plurality of operating mode selection keys, and in which on actuating at least one of the operating mode selection keys, at least one and preferably a plurality of the switching keys are blocked.

The predetermined proportion of the switching keys can amount to up to 100% in one or more operating modes, but not, however, in all operating modes, in which case no switching key is blocked. However, in accordance with the invention, at least one of the switching keys is blocked in at least one operating mode.

The concept underlying the invention is thus to be seen in the fact that numerous switching keys satisfy a double function in that they trigger different characteristics depending on the just selected operating mode, without the operator himself having to make a selection in this respect. Thus, for example, one and the same switching key is used in order to select an individual characteristic, both for monopolar coagulation and also for tripolar and bipolar coagulation. The operator thereby only needs to press the desired operating mode selection key and the switching key corresponding to the desired characteristic. The ideal current-voltage characteristic for the selected coagulation process is then made available inside the apparatus for the selected operating mode, depending on the operating mode.

The invention can be particularly advantageously used when a plurality of functions is also preset apart from the plurality of operating modes and characteristics, with a special set of switching keys being associated with each function. The functions are expediently selected by switching at the instrument itself.

When actuating one of the switching keys or one of the operating mode selection keys, the remaining keys are blocked in order that a multiple actuation of the switching keys or operating mode selection keys is prevented in each case. The operating mode selection keys can be expediently designed as individual keys, rotary switching keys and/or sequence switching keys. A sequence switching key is to be understood to mean that numerous individual keys are combined into a sequence switching key, with the circuits corresponding to the pressing of a single key being selected one after the other with a sequence switching key by multiple pressing of the sequence switching key. Display lamps are provided above the switching sequence key. The number of display lamps corresponds to the number of possible switching processes. In this arrangement the display lamps preferably indicate the switching state in which the switch acted on by the sequence switching key is to be found.

The dialing in of the individual keys should preferably be made outwardly recognizable with an indicator device or lamp.

With a display device, in particular, a luminous field associated with each switching key, the operator is shown in a clear manner on the switching and display field which keys can be selected and which are blocked.

The operating modes can be of a technical process nature or in a nature of technical applications. With a subdivision into technical processes, a monopolar, tripolar or bipolar mode of operation can preferably be selected. An application for a subdivision in accordance with technical applications provides for gynecological, urological and endoscopic modes of operation.

Since a specific treatment instrument is respectively associated with each operating mode selection switch, the invention provides for further functions which relate to the selected treatment instrument to be triggered on dialing in a specific operating mode, such as, for example, a display of the readiness of operation at the associated instrument.

Since, with high-frequency surgical apparatus, the switching on of an instrument is frequently effected by an external switch, particularly by a foot switch, the present invention provides that by the dialing of a specific operating mode, the external switch is simultaneously associated with the instrument dialed in by the operating mode selection key so that no form of manipulation needs to be effected by the surgeon in order to correctly connect the external switch.

High-frequency surgical apparatus generally include the monopolar mode of operation in which, apart from the actual treatment instrument, a neutral electrode is also connected which is brought into contact with the body of a patient at a suitable position. The neutral electrode is normally connected within the apparatus to an alarm device which responds when the neutral electrode is not in electrical contact with the body of a patient or is not in problem-free electrical contact with the body of a patient. If a high-frequency surgical apparatus of this kind is used in an operating mode other than the monopolar operating mode, the neutral electrode is not required, and is thus not in contact with the patient. Since it nevertheless frequently remains connected to the apparatus, the problem exists that the alarm device responds and simulates non-problem-free functioning of the apparatus.

For this reason the invention provides, that this alarm device can be made inactive automatically by a suitable connection to the electronics on which the operating mode selection keys act when the monopolar operating mode is departed from by the selection of an operating mode different from the monopolar operating mode.

DESCRIPTION OF PREFERRED EXEMPLARY EMBODIMENTS

Figure 1:
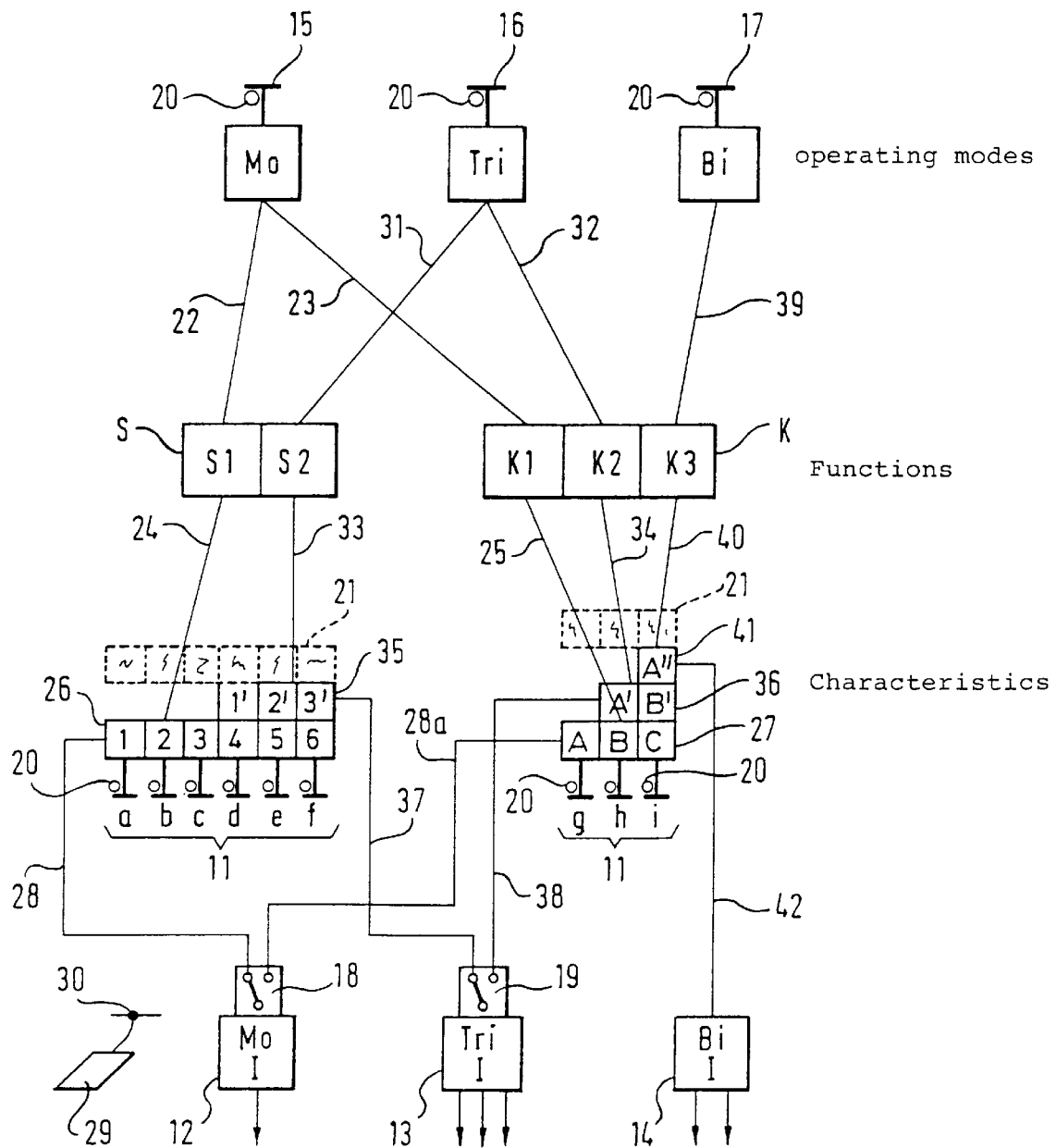
FIG. 1 is a schematic representation of a high-frequency surgical apparatus in accordance with the invention.

In accordance with FIG. 1, a high-frequency surgical apparatus in accordance with the invention has three operating mode selection keys 15, 16, 17 for the operating modes monopolar, tripolar and bipolar respectively, which are accessible from an operating field or panel at the front side.

The signals formed on actuation of the operating mode selection key 15 address, via paths 22, 23, respective function blocks S1 and K1, which stand for the functions cutting and coagulation.

Signal paths 24, 25 lead from the function blocks S1 and K1 to modification blocks 26 and 27. The modification blocks 26 and 27 can be selected by six switching keys 11a, b, c, d, e, f and by three switching keys 11g, h, i respectively, which are accessible from the front side of the apparatus.

Signal paths 28a and 28 lead from the modification blocks 26, 27 to a changeover switch 18 arranged on a monopolar treatment instrument 12 which can be actuated by an operator. The changeover switch makes it possible to selectively connect the signal path 28 or the signal path 28a to the treatment instrument 12. The neutral electrode 29, which belongs to the monopolar treatment instrument 12, is connected to the apparatus in a suitable manner at 30.

In a corresponding manner, a signal path 31 leads from the operating mode selection key 16 to a function block S2 for cutting. A signal 32 leads to a function block K2 for coagulation. From these function blocks S2, K2 signal paths 33 and 34 respectively lead to modification blocks 35 and 36 which are respectively controlled via the switching keys 11d, e, f, and 11h, i. Signal paths 37, 38 extend from the modification block 35, 36 to a changeover switch 19 provided on a tripolar treatment instrument 13. The changeover switch 19 can be actuated by the operator and permits the instrument to be selectively connected to one of the modification blocks 35 or 36.

Finally, the operating mode selection key 17 is connected via a signal path 39 to a function block K3 for coagulation, from where a further signal path 40 extends to a single modification block 41, which is controlled by the switching key 11i. A signal path 42 leads from the modification block 41 to a bipolar treatment instrument 14 connected to the apparatus. A respective display lamp 20 is associated with each switching key 15, 16, 17 and 11a to 11i and lights up when the relevant switching key is pressed and is not blocked in the manner which results from the following description.

A luminous field 21 is, moreover, associated with each of the switching keys 11a to 11i and lights up when the relevant switching key can be selected and is not blocked, and indeed independently of whether the switching key is actuated or not.

The function blocks S1, S2 jointly form a function block arrangement S, the function blocks K1, K2 and K3 jointly forming a function block arrangement K.

The modification blocks 26, 35, 27, 36, 41 each have electronic stages 1, 2, 3, 4, 5, 6; 1', 2', 3'; A, B, C; A', B'and A" respectively, which modify the high frequency intended for the particular attached instrument in such a way that an ideally suited graduation of high frequency characteristics, i.e. impedance dependent, high-frequency, current-voltage characteristics is achieved for the relevant instrument.

The manner of operation of the high-frequency surgical apparatus described is as follows:

If the operating selection key 15 is pressed, then the modification blocks 26 and 27 are activated via the function blocks S1 and K2, which means that the switching keys 11a to 11f, can dial in the electronic stages 1, 2, 3, 4, 5, 6 and the switching keys 11g, h, i can dial in the electronic stages A, B and C respectively within the non-illustrated high-frequency generator. In accordance with the invention, only one of the switching keys 11a to f or 11b to i can in each case be actuated. After such an actuation, the remaining switching keys of the two sets of switching keys are blocked.

Whereas the function blocks S1 and K1 take account of and realize the electronic requirements for the functions cutting and coagulation respectively, the electronic stages 1–6 and A–C of the modification blocks 26 and 27 respectively make available the characteristic of the impedance dependent, high-frequency, current-voltage characteristic required for the desired operation of the instrument. It is primarily the functional dependence of the power on the impedance and/or the modulation of the high frequency that is used that is altered. The electronic function blocks S1 and K1 respectively, and also the electronic stages 1 to 6 and A to C, are respectively matched entirely to the requirements of the monopolar treatment instrument 12 and modify the parameters which are generated by the non-illustrated high-frequency generator in a predetermined manner.

After the pressing of the operating selection key 15 the remaining operating selection keys 16 and 17 are blocked.

If now the tripolar treatment instrument 13 is to be operated, then only the operating selection key 16 is pressed, whereby the previously switched on operating mode is first deactivated, and the electronic function blocks S2 and K2 respectively, and also the modification blocks 35 and 36 respectively, are activated, of which the electronic stages 1', 2', 3'and A', B' respectively can be dialed in, i.e. selected via the switching keys 11d, e, f and 11h, i respectively. Thus, in accordance with the invention, the electronic stages 1', 2', 3' and A', B' are dialed in or selected by the same switching keys 11d, e, f and 11h, i as the above-named electronic stages 4, 5, 6 and A, C respectively. Thus, the same set of switching keys 11 is used for two different modification blocks 26 and 35 respectively and 27 and 36 respectively.

Since the tripolar treatment instrument 13 only requires three different graduations of the characteristic of the high frequency, current-voltage characteristic in the operating mode "cutting", and only two graduations in the operating mode "coagulation", the switching keys 11a, b, c and 11g are blocked in accordance with the invention on pressing the switching key 16. This is shown in the associated luminous fields 21 in that these do not light up, whereas the luminous fields 21, which are associated with the electronic stages 1', 2', 3'and A', B' light up on activation of the relevant switching key blocks 35, 36 and preferably symbolically represent the treatment processes which are now possible by intentional pressing of the switching keys.

By changing over the keys 18 and 19, it is possible to select whether the key fields 11a to 11f or 11g to 11i are made effective in the all-embracing form 26, 27 or in the restricted form 35, 36.

The third possibility with the embodiment shown in FIG. 1 lies in the bi-polar operating selection key 17 being pressed, whereupon a further modification block 41 is activated via the signal path 39, an electronic function block K3 and the signal path 40, with the further modification block 41 having, in this embodiment, only a single electronic stage A" which can be dialed in from the same switching key 11i as the electronic stages B' and C'. During dialing the electronic stage A" acts via the signal path 42 on the bipolar treatment instrument 14 and supplies it with a suitable high-frequency current-voltage plot.

Figure 2:
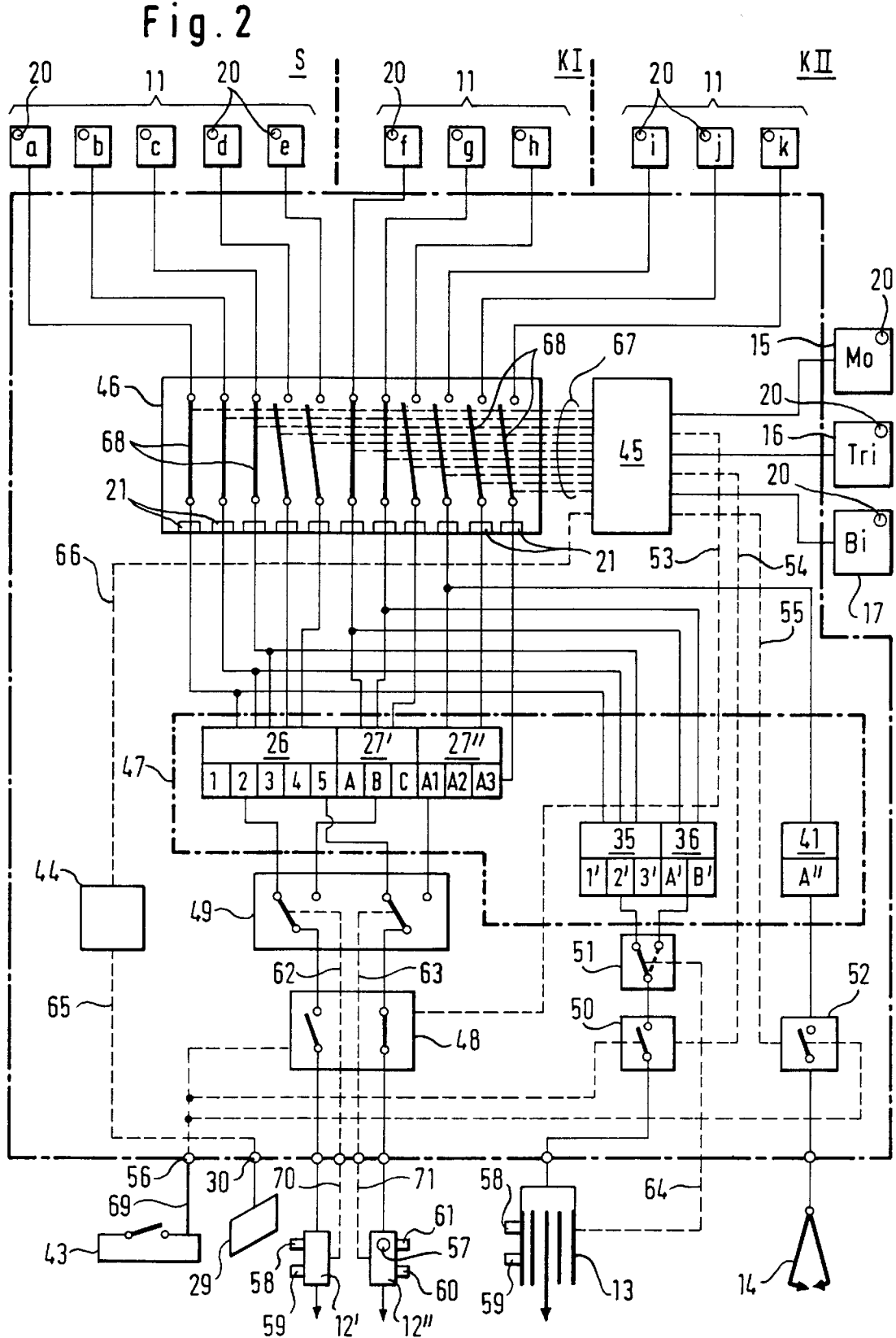
FIG. 2 is a practical embodiment of a high-frequency surgical apparatus in accordance with the invention, likewise in a schematic representation in the form of a block circuit diagram.

In the embodiment of FIG. 2, the same reference numerals designate elements which correspond to those in FIG. 1.

In accordance with FIG. 2, the operating mode keys 15, 16, 17 are connected to an electronic circuit 45 which acts via a control line set 67 on a key blocking/unblocking stage 46, which contains individually controlled on-off-switches 68 for each switching key 11a to 11k. The switching keys 11a to 11k are connected to the individual switches 68 of the key blocking/unblocking stage 46 so that a predetermined number of switching keys 11 is switched through or blocked, in dependence on the depressed operating mode selection key 15, 16 or 17 and the switches 68 which are individually opened or closed thereby. The switching keys 11a to 11e are associated with the function S "cutting", the switches keys 11f to 11h are associated with a function K1 "coagulation" and the switching keys 11i to 11k are associated with a second function K2 "coagulation".

In the switching position of the stage 46 reproduced in FIG. 2, it is assumed that the operating mode selection key 16 for the tripolar instrument 13 has been depressed, which leads to a dialing in of the switching keys 11a, b, c of the function mode S and of the switching keys 11f, g of the function mode K1. The remaining switching keys 11d, e and h, i, j and k are in this case blocked by opening of the corresponding switches 68 in the stage 46.

In the actual high-frequency generator 47, which is bounded by a chain dotted line, there are provided, among other things:

a modification block 26 with electronic stages 1, 2, 3, 4, 5;

a modification block 27' with electronic stages A, B, C;

a modification block 27" with electronic stages A1, A2 and A3;

a modification block 35 with electronic stages 1', 2', 3';

a modification block 36 with electronic stages A', B', and a modification block 41 with an electronic stage A".

In distinction to the block circuit diagram illustrating the principle in FIG. 1, the modification block 26 of FIG. 2 has only five electronic stages 1 to 5 delivering different characteristics. Moreover, two different modification blocks 27', 27" with respective electronic stages A, B, C and A1, A2, A3 having different characteristics, are respectively associated with the switch key sets 11f to 11h and 11i to 11k for the functional mode "coagulation".

In further distinction to FIG. 1, two monopolar treatment instruments 12', 12" are connected to the high-frequency surgical apparatus in accordance with FIG. 2 and are connected to the modification blocks 26, 27', 27" via a changeover switch 48 and a function selection switch 49 in the manner shown in FIG. 2.

The tripolar treatment instrument 13 is connected via a switching device 50 and a function selection switch 51 to the modification blocks 35, 36. Finally, a bipolar treatment instrument 14 connected to the apparatus is connected via a switching device 52 to the modification block 41.

In FIG. 2, control lines 53, 54, 55 shown in broken lines lead from the electronics 45 to the switching devices 48, 50 and 52 respectively which, on pressing of the associated operating mode selection key 15, 16, or 17, connect the respective treatment element 12', 12", 13 or 14 to the high frequency generator 47. Since two treatment instruments 12', 12" are connected to the changeover device 48, the switching device 48 is, moreover, so designed that only one of the two monopolar treatment instruments 12', 12" is connected in each case and indeed preferably the one which is first actuated by the acting surgeon.

Furthermore, the foot switch 43 provided for the switching on and off of the respectively attached treatment instrument 12', 13' or 14 is schematically illustrated in FIG. 2 and is connected via a cable 69 to a socket 56 of the apparatus.

The foot switch 43 is selectively connectable to one of the treatment instruments 12' or 12", 13, 14, which is likewise caused by the electronic circuit 45, which reacts to the depressing of the operating mode selection keys 15, 16, 17, likewise via the control lines 53, 54, 55. In this manner, a situation is achieved in which the foot switch 43 is in each case automatically connected to that treatment instrument which is to be operated as a result of selecting the associated operating mode selection key 15, 16 or 17.

With respect to the treatment instruments 12', 12" it can previously be specified which of the two instruments is to be actuated by the foot switch 43 and which is to be actuated by a hand switch 57 which is, for example, present on the instrument 12".

Finally, FIG. 2 also indicates by the broken lines 62, 63 how the function selection switch 49 can be changed over into the position "cutting" and "coagulation" by means of switch buttons 58, 59 or 60, 61 provided at the treatment instrument 12', 12". Switch buttons 58, 59 and 60, 61 are effective via control lines 70, 71 extending to the function selection switch 48.

The tripolar treatment instrument 13 also has two such switch buttons 58, 59 which can place the function selection switch 51 in the position "cutting" or "coagulation" via a control line 64.

Furthermore, FIG. 2 also indicates the neutral electrode 29 for the monopolar cutting, which is connected at 30. The energization of the neutral electrode by high frequency is not shown in detail. However, a control line 65 indicated in broken lines is shown, which leads to an alarm device 44, which is moreover acted on by a further control line 66 from the electronic circuit 45.

The alarm device 44 responds in the monopolar operating mode when the neutral electrode 29 is not in electrical contact with the body of a patient or is not in problem-free electrical contact with the patient's body. Since this is generally the case in the operating modes tripolar and bipolar, the electronic circuit 45 ensures that the alarm device 44 is deactivated when the operating mode selection key 15 is not depressed. In this manner the alarm device 44 is switched off when the operating mode selection keys 16, 17 are pressed and with corresponding deactivation of the operating mode selection key 15.

As already mentioned, two switching key sets 11f, g, h and 11i, j, k are provided in the embodiment of FIG. 2 for two functional modes K1 and K2 respectively. The switching keys 11f, g are thereby connected to the tripolar instrument 13 in case of activation of the tripolar operating mode, whereas, of the switching key set 11i, g, k, only the switching key 11i is connected to the modification block 41 of the bipolar treatment element 14 on pressing the bipolar operating mode selection key 17. One of the switching keys 11f, g, h could basically also be used for this purpose.

In accordance with the invention, there is the provision of two sets of switching keys for the function mode K1 "coagulation" and for the function mode K2 "coagulation." With the simultaneous connection of two monopolar treatment instruments 12', 12", an individual modification block 27' and 27" is available for each instrument 12', 12" respectively. In this way the treatment instruments 12', 12" are influenced by the same modification block 26 in the "cutting" mode so that the cutting characteristics of both instruments are the same. However, for the coagulation, different characteristics for the two treatment instruments 12', 12" can be provided in the coagulation mode in the electrode stages A, B, C and A1, A2, A3 respectively. This represents a substantial advantage because in this way, with a specific operation, two treatment instruments 12', 12" are available and different requirements with respect to their characteristics can be satisfied during coagulation.

It should be emphasized that in the event that all instruments are connected in the manner shown in FIG. 2, it is always only one of the instruments which can be in operation at a particular time. This is brought about by pressing the corresponding operating mode selection key. By pressing the operating mode selection key 15, the two treatment instruments 12', 12" can be dialed in. However, provision is made inside the apparatus that it is always only the first instrument which is switched on which is in operation, whereas the other is automatically kept in the switched off state.

As a result of the enlarged arrangement of FIG. 2, it is also possible for the operating mode selection keys 15, 17 to be also dialed in simultaneously, since in this case the switching keys 11a, b, c, d, e; 11f, g, h for the monopolar treatment instrument 12' or 12" and 11i for the bipolar treatment instrument 14 are unblocked so that when the treatment instruments 12', 12" and 14 are connected, three instruments are ready for use without the actuation of a further operating mode selection key being required.

As a result of the same consideration, the operating mode selection keys 16, 17 could also be simultaneously pressed because then the situation likewise exists in which only switching keys 11 which are decoupled from one another can be dialed in.

In other respects the manner of operation of the embodiment of FIG. 2 is the same as that described with reference to FIG. 1.

What is claimed is:

1. A high-frequency surgical apparatus capable of operating in a plurality of different operating modes, including monopolar, tripolar and bipolar, and capable of performing at least one function in each operating mode, the apparatus being capable of performing a plurality of functions in at least one of the operating modes, the apparatus comprising:

an operating mode selection key for each operating mode;

a plurality of switching keys, at least a proportion of the switching keys being associated with a plurality of operating mode selection keys;

a plurality of instruments, each instrument associated with a respective operating mode;

a display device associated with each switching key; and a function selection switch for each instrument capable of performing different functions, the function selection switch allowing different and independent functions within an operating mode associated with the respective instrument to be selected;

wherein upon actuating at least one of the operating mode selection keys, at least one of the switching keys is blocked;

wherein at least one characteristic within each function may be dialed in by a switching key; and wherein the display device indicates whether the associated switching key may be selected in the switched-on operating mode or is blocked.

2. A high-frequency surgical apparatus in accordance with claim 1, wherein upon actuating at least one of the operating mode selection keys, a plurality of the switching keys are blocked.

3. A high-frequency surgical apparatus in accordance with claim 1, wherein for each instrument capable of performing different functions, the respective function selection switch is located at the instrument itself.

4. A high-frequency surgical apparatus in accordance with claim 1, wherein each of the switching keys is configured such that upon actuating one of the switching keys, the remaining switching keys associated with the remaining operating mode selection keys are blocked.

5. A high-frequency surgical apparatus in accordance with claim 1, wherein the operating mode selection keys consist of at least one type of key from a group consisting of individual keys, rotary switching keys, and sequence switching keys.

6. A high-frequency surgical apparatus in accordance with claim 1, wherein the switching keys are configured to each individually control an electronic switching stage that results in a characteristic desired in connection with a selected operating mode and function.

7. A high-frequency surgical apparatus in accordance with claim 1, wherein the operating mode selection keys and the switching keys are connected via a databus to a microcontroller that dials in characteristics selected by key pressure and handles an appropriate feeding of the associated instrument.

8. A high-frequency surgical apparatus in accordance with claim 1, further comprising a plurality of indicator devices, each indicator device being associated with a respective operating mode selection key or respective switching key, each indicator device being configured to respond when its associated operating mode selection key or switching key is pressed, thus indicating that the relevant operating mode or characteristic has been selected.

9. A high-frequency surgical apparatus in accordance with claim 8, wherein the indicator devices are indicator lamps.

10. A high-frequency surgical apparatus in accordance with claim 1, further comprising an external switch connected to each instrument for switching on or switching off the instruments, the external switch being associated with the instruments by actuation of the operating mode selection keys.

11. A high-frequency surgical apparatus in accordance with claim 10, wherein the external switch is a foot switch.

12. A high-frequency surgical apparatus in accordance with claim 1, wherein the apparatus is capable of operating in a monopolar operating mode, the apparatus further comprising an alarm device and a neutral electrode, wherein the alarm device responds when the neutral electrode is not in a trouble-free electrical contact with a patient, and wherein the alarm device is made inactive upon deactivating the monopolar operating mode.

* * * * *